(12) United States Patent
Leblanc

(10) Patent No.: US 10,393,720 B2
(45) Date of Patent: Aug. 27, 2019

(54) SYSTEM AND METHOD FOR DYNAMICALLY LOCATING A FAULT OBSERVED ON A COMPONENT

(71) Applicant: SAFRAN AIRCRAFT ENGINES, Paris (FR)

(72) Inventor: Jonathan Leblanc, Paris (FR)

(73) Assignee: SAFRAN AIRCRAFT ENGINES, Paris (FR)

( * ) Notice: Subject to any disclaimer, the term of this patent is extended or adjusted under 35 U.S.C. 154(b) by 548 days.

(21) Appl. No.: 14/357,900

(22) PCT Filed: Nov. 21, 2012

(86) PCT No.: PCT/FR2012/052682
§ 371 (c)(1),
(2) Date: May 13, 2014

(87) PCT Pub. No.: WO2013/076421
PCT Pub. Date: May 30, 2013

(65) Prior Publication Data
US 2014/0288857 A1 Sep. 25, 2014

(30) Foreign Application Priority Data
Nov. 23, 2011 (FR) .................................. 11 60699

(51) Int. Cl.
*B21J 5/00* (2006.01)
*G01N 33/20* (2019.01)
(Continued)

(52) U.S. Cl.
CPC ................ *G01N 33/20* (2013.01); *B21J 5/00* (2013.01); *G01N 29/043* (2013.01);
(Continued)

(58) Field of Classification Search
CPC .. B21J 5/00; B21J 7/00; G01N 29/043; G06T 7/001; G06T 2207/30136; G06T 2207/30164
(Continued)

(56) References Cited

U.S. PATENT DOCUMENTS 5,337,611 A 8/1994 Fleming et al.
6,487,468 B1 11/2002 Atsumi et al.
(Continued)

FOREIGN PATENT DOCUMENTS

JP 2000-197942 7/2000

OTHER PUBLICATIONS

International Search Report dated Mar. 15, 2013 in PCT/FR12/052682 Filed Nov. 21, 2012.

*Primary Examiner* — Leslie J Evanisko
(74) *Attorney, Agent, or Firm* — Oblon, McClelland, Maier & Neustadt, L.L.P.

(57) ABSTRACT

A method and system for dynamic locating of a fault observed in a defective component related to a forging operation, in which: a processor models a shaping operation of a component by forging, as per a set of successive models of the component; a processor adds a fault plotter to a first model of the set of models, in a zone corresponding to a region of the fault in the defective component to obtain a first plotted model; and a processor tracks the plotter in time from the first plotted model during the modelling to locate an origin of the fault.

12 Claims, 9 Drawing Sheets

(51) Int. Cl.
G01N 29/04 (2006.01)
G01N 29/44 (2006.01)
G06T 7/00 (2017.01)

(52) U.S. Cl.
CPC ......... *G01N 29/4472* (2013.01); *G06T 7/001* (2013.01); *G01N 2291/0251* (2013.01); *G06T 2207/30136* (2013.01); *G06T 2207/30164* (2013.01)

(58) Field of Classification Search
USPC .......................................................... 702/35
See application file for complete search history.

(56) References Cited

U.S. PATENT DOCUMENTS

| | | |
|---|---|---|
| 6,776,212 B1 | 8/2004 | Fulton et al. |
| 7,092,484 B1 | 8/2006 | Jensen et al. |
| 2004/0073401 A1* | 4/2004 | Batzinger ............... B21C 51/00 702/181 |
| 2004/0261968 A1 | 12/2004 | Fulton et al. |
| 2008/0156451 A1 | 7/2008 | Fulton et al. |
| 2010/0132905 A1 | 6/2010 | Fulton et al. |
| 2011/0203759 A1 | 8/2011 | Fulton et al. |
| 2012/0193060 A1 | 8/2012 | Fulton et al. |

* cited by examiner

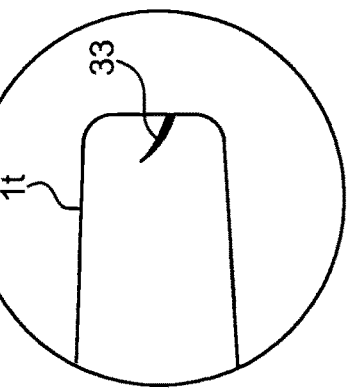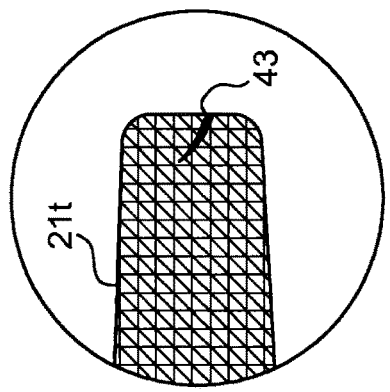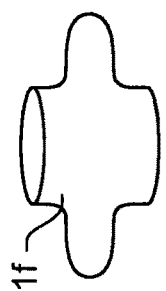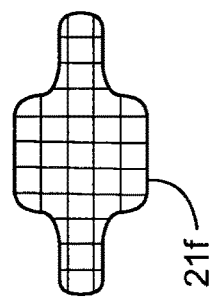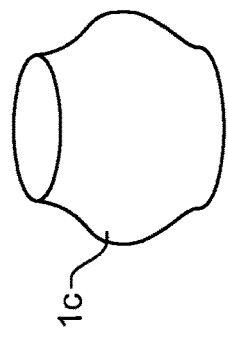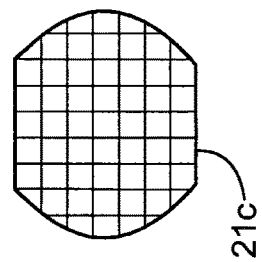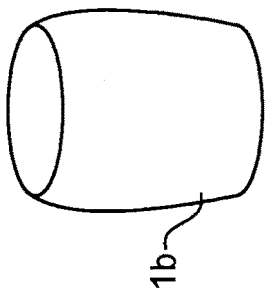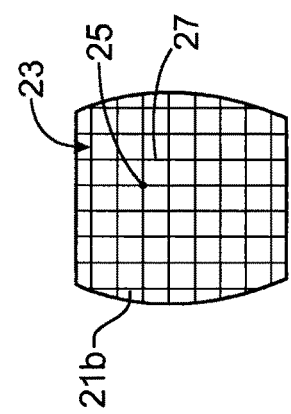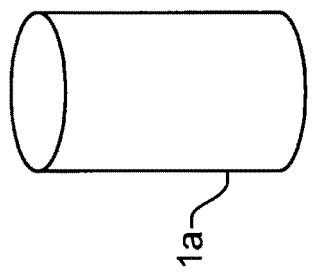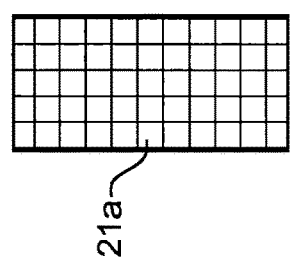
FIG.3

SYSTEM AND METHOD FOR DYNAMICALLY LOCATING A FAULT OBSERVED ON A COMPONENT

TECHNICAL FIELD

The present invention relates to the general field of forging and concerns the dynamic locating of a fault found in a defective component resulting from the forging operation. It finds application in all industrial fields and in particular in the field of aeronautics in which forged components are subjected to maximum constraints of quality and safety.

STATE OF THE PRIOR ART

At the time of shaping forged components, fluctuation in production may lead to the forming of defects potentially causing the rejection of these components. The detection of defects in forged components can be performed using inspection means of ultrasound, magnetic detection or visual type.

The cause of a defect may be related to forging parameters or to faulty configuration of forming tools. It is therefore important to identify or locate the origin of a defect to improve the forging operation or tooling.

At the current time, to identify the origin of a defect in a forged component, the defect is approximately related to the original part before forging. This relating of defects is imprecise and is performed solely for defects present on the surface and in regions having easy visual identification.

In addition, with this type of comparison it is not possible to locate a defect generated during an intermediate forging step and it is not possible to analyse propagation of the defect, which is detrimental to good diagnosis of defects.

The objective of the present invention is therefore to propose a system and method for the dynamic locating of a defect or fault observed in a defective component, which overcome the aforementioned drawbacks and provide prospective or retrospective knowledge of the propagation of the defect.

DESCRIPTION OF THE INVENTION

The present invention is defined by a system for the dynamic locating of a fault observed in a defective component related to the forging operation, comprising:
processing means to model a component shaping operation by forging, using a set of successive models of the said component;
processing means to add a fault plotter to a first model of said set of models in a zone corresponding to the region of the fault of the said defective component to obtain a first plotted model; and
processing means to track the said fault plotter over time during the said modelling from the said first plotted model to locate the origin of the said fault.

It is thus possible prospectively or retrospectively to diagnose the propagation of the fault in the medium of the component.

Advantageously, the dimensions and position of the zone associated with the said fault plotter in the first model are substantially similar to the dimensions and position of the fault region in the defective component.

According to one particular embodiment of the present invention, the modelling of the shaping operation is dynamic modelling using finite elements forming at each modelling time step a polygonal mesh representing the component at the corresponding forging step.

Advantageously, the processing means are configured to define at each modelling time step the dimensions and position of the said fault plotter as a function of the elementary elements of the said mesh at the said step in time.

According to a first embodiment of the present invention, the said set of successive models comprises an initial model corresponding to the component before forging, intermediate models corresponding to intermediate forging steps, and a final model corresponding to the forged component, the said first model corresponding to the said final model and the first plotted model corresponding to a final plotted model, the processing means being configured to track the said fault plotter in time by reversing the sequence of the said modelling starting from the said final plotted model.

The processing means are configured to locate the said fault plotter in the initial model to identify the region in which the fault would have been in the component before forging.

Advantageously, the processing means are configured to locate the said fault plotter in intermediate models comprising particular configurations to verify whether the said particular configurations are likely to induce the said fault.

According to a second embodiment of the present invention, the said set of successive models comprises an initial model corresponding to the component before forging and a final model corresponding to the forged component, the said first model corresponding to the said initial model and the said first plotted model corresponding to an initial plotted model, the processing means being configured to locate the said fault plotter in the final model to verify whether the fault in the forged component lies outside a machining region of the said forged component.

Advantageously, the said fault plotter is a contrast element associated with the said polygonal mesh.

The invention also concerns a method for the dynamic locating of a fault observed in a defective component related to a forging operation, comprising the following steps:
modelling an operation to shape a component by forging as per a set of successive models of the said component;
adding a fault plotter, to a first model of said set of models, in a zone corresponding to the region of the fault of the said defective component, to obtain a first plotted model; and
tracking the said fault plotter over time during the said modelling starting from the said first plotted model to locate the origin of the said fault.

BRIEF DESCRIPTION OF THE DRAWINGS

A description will now be given of non-limiting examples of embodiments of the invention with reference to the appended Figures in which:

FIG. 3 schematically illustrates a set of successive models of the shaping of the component, according to the invention.

DETAILED DESCRIPTION OF PREFERRED EMBODIMENTS

The concept at the base of the invention is the use of modelling of component shaping to track propagation of the fault.

Figure 1:
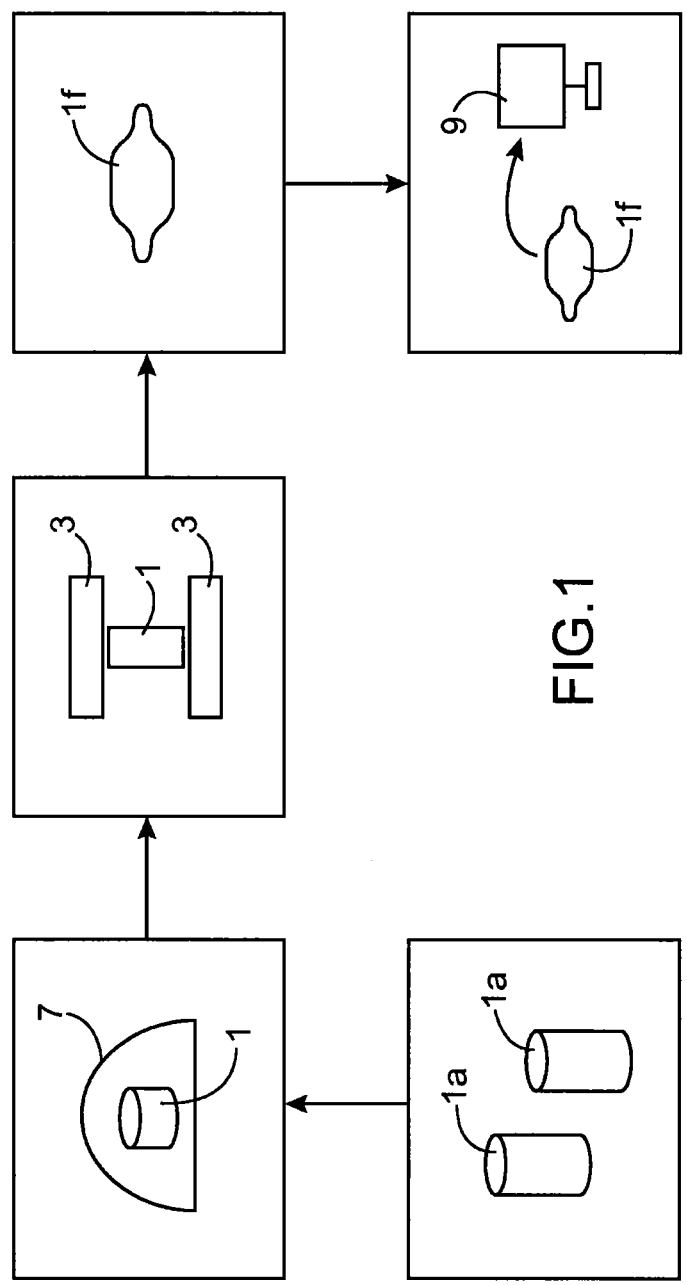
FIG. 1 schematically illustrates a forging process.

FIG. 1 schematically illustrates a forging process.

The components to be forged which are generally of cylindrical shape called ingots or blanks 1a are hot or cold worked between two dies or forging tools 3 by hammering or pressure using a forging press, to form forged components. The final component 1f often resembles a large disc or dish of particular geometry.

For hot working, the component 1 is placed in a furnace 7 before the flattening step and in some cases the forging and flattening steps are repeated several times before obtaining the final component 1f.

On completion of forging, inspection is carried out using ultrasound, magnetic detection or visual means 9 to verify that a forged component 1f does not comprise any faults before starting a machining operation for example on this component 1f.

The present invention proposes locating the fault dynamically to identify the origin thereof. This makes it possible for example to determine whether the fault is isolated or reproducible on a series of components and in this case corrective action can be performed to avoid the reproduction of this fault.

Figure 2:
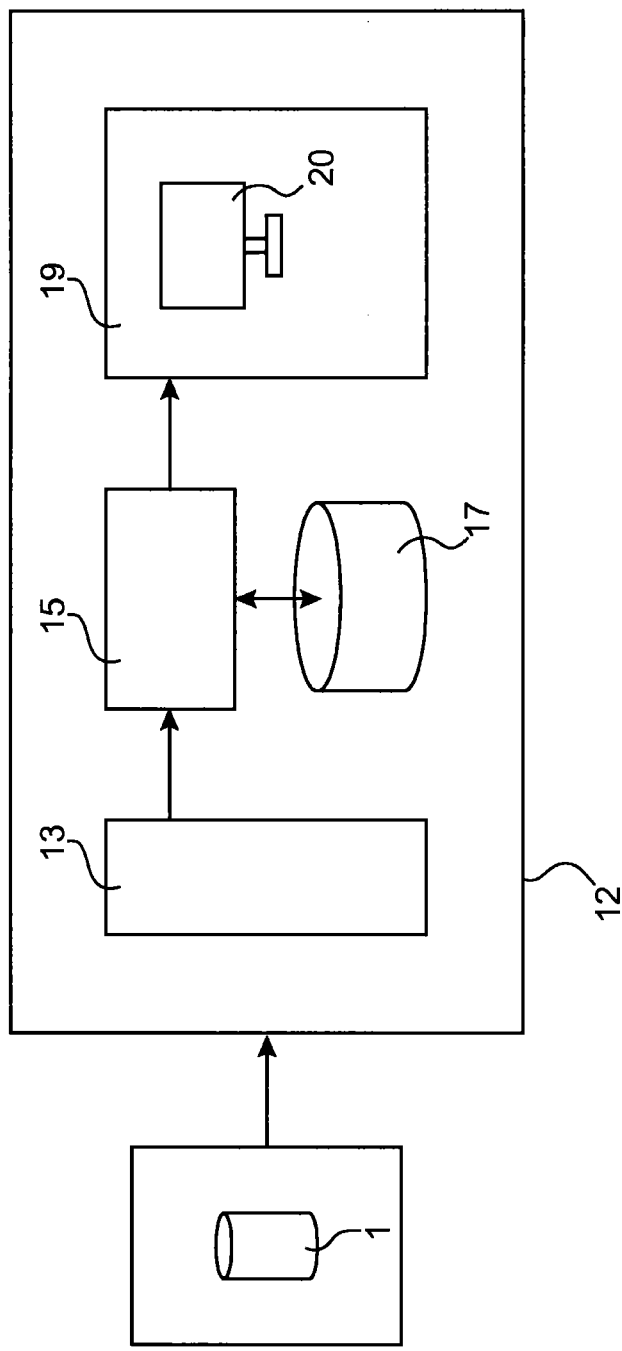
FIG. 2 schematically illustrates a system 12 for the dynamic locating of a fault observed in a defective component 1, according to the invention.

FIG. 2 schematically illustrates a system 12 for the dynamic locating of a fault observed in a defective component 1 according to the invention.

By dynamic locating of a fault is meant the time-space identification of the fault in relation to the space taken up by the component 1 and at successive times of its shaping. In other words, it is the spatial locating of the fault in the component 1 at every moment of its transformation.

The locating system 12 comprises data input means 13, processing means 15, storage means 17 and output means 19 comprising viewing means 20. The processing means 15 allow the execution of one or more computer programmes comprising programme code instructions stored in the storage means 17 and designed to implement the method for dynamically locating a fault.

More particularly, the processing means 15 are configured to model the shaping operation of a component 1 by forging in accordance with a set of successive models of the component.

FIG. 3 schematically illustrates a set of successive models 21a-21t of the shaping of the component 1 comprising an initial model 21a representing the blank 1a (i.e. the component before forging), intermediate models 21b, 21c representing intermediate forged components 1b, 1c, and a final model 21f representing the forged component 1f (i.e. the final component after forging).

It will be noted that modelling can be conducted in three dimensions (3D) or optionally in two dimensions (2D) for axisymmetric components.

Therefore, the processing means 15 are used for the numerical solving of equations modelling the working of the component 1 under the action of forging tools 3 in relation to forging parameters e.g. comprising a temperature range of the component 1 and of the tooling 3, a pressure range, heat transfer coefficients, the density of the component 1, a range of working speed, etc. These parameters allow numerical modelling to best represent actual forging operations in the workshop. For example, the heat transfer coefficients allow heat dissipated by the component 1 into the surrounding medium during the forging operation due to radiation and/or convection to be taken into account, and in particular when the temperature of the component 1 is high (e.g. in the order of 1000° C.).

Numerical solving is conducted iteratively and for example uses meshes 23 to discretise the continuous geometric domain of the component using finite elements described by vertices or nodes 25 and edges 27. Therefore dynamic modelling via finite elements, at each iteration or modelling step in time, forms a polygon mesh 23 (e.g. triangular) which represents the component 1 at the corresponding forging step.

When a fault 33 is observed in a defective component 1t, data is recorded relating to the fault 33 (e.g. the dimensions and position of the fault in the component 1t) and these data are imported into the dynamic locating system 12.

The input means 13 of the dynamic locating system 12 are used to input data relating to the fault 33 and enable the processing means 15 to insert an equivalent of the fault 33 into the model 21t corresponding to the defective component 1t.

More specifically the processing means 15 are configured so that, to a first model 21t belonging to the set of models 21a-21t of the forging operation, they add a fault plotter 43 in a zone corresponding to the region of the fault in the defective component it to obtain a first plotted model 21t. In other words, the first plotted model 21t represents the defective component it at the time the fault is detected.

Advantageously, the zone associated with the fault plotter 43 in the first model 21t has substantially similar dimensions and positioning to the dimensions and position of the fault region 33 in the defective component 1t.

The processing means 15 together with the viewing means 20 then allow the tracking in time of the fault plotter 43 during modelling starting from the first plotted model 21t to diagnose the dynamics of the fault 33. In this manner the propagation of the fault 33 in the component 1 can be tracked prospectively (i.e. moving forward in time) or retrospectively (i.e. going back in time) starting from the first plotted model 21t.

In particular, at each modelling time step the dimensions and position of the fault plotter 43 can be defined as a function of the elementary elements (i.e. nodes 25 and/or edges 27) of the mesh 23 at the current time step.

For example, the fault plotter 43 is a contrast element which represents the fault 33 in terms of dimension and position and which can be integrated into the corresponding polygon mesh 23 of the model 21 using a known technique of CAD type. For example, the fault plotter 43 can be represented by a coloured contour contrasting with the mesh 23, enclosing a surface substantially equal to the surface of the actual fault 33, and defined in relation to nodes 25 in the vicinity of the fault. It will be noted that it is not necessary to have knowledge either of the type or of the precise shape of the fault 33.

FIGS. 4 and 4A-4D illustrate a method for dynamically locating a fault detected in a defective component, according to one preferred embodiment of the invention.

According to this embodiment, the first model to which the fault plotter is added corresponds to the final model 21f representing the forged component 1f, so that the first plotted model 21t corresponds to a final plotted model 21tf representing a defective forged component 1tf.

At step E1 the processing means 15 model the shaping operation of a component by forging 1 in accordance with successive models 21a-21f comprising an initial model 21a corresponding to the component before forging (blank) 1a and a final model 21f corresponding to the forged component 1f.

Figure 4:
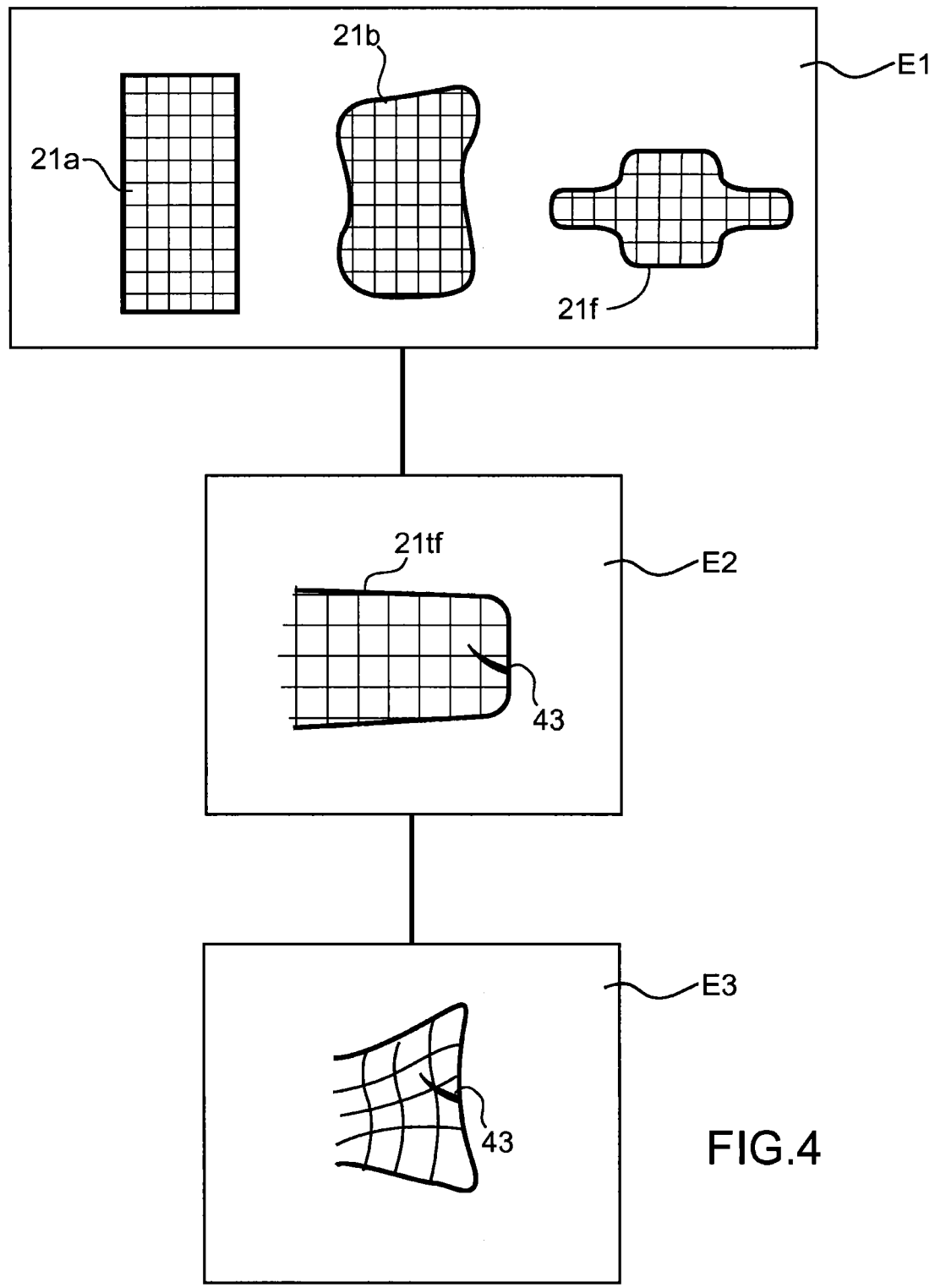
FIGS. 4 and 4A-4D illustrate a method for dynamically locating a fault observed in a defective component, according to one preferred embodiment of the invention.
Figure 4A:
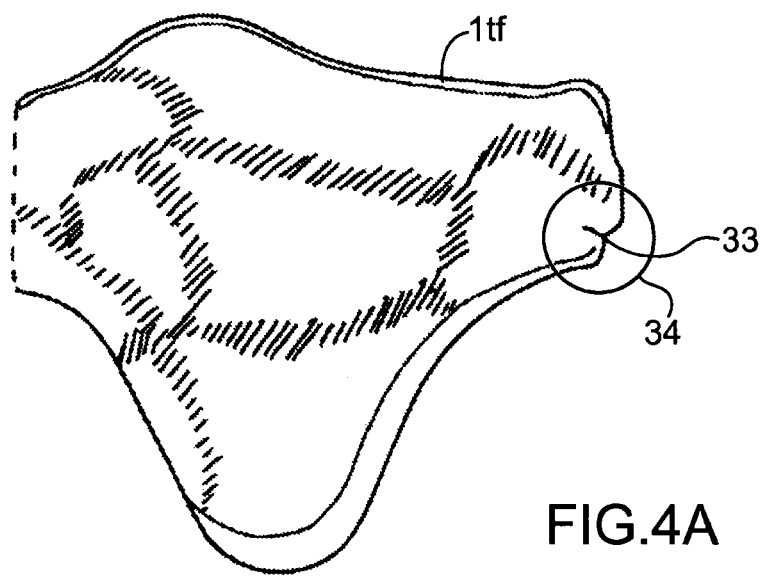
Figure 4B:
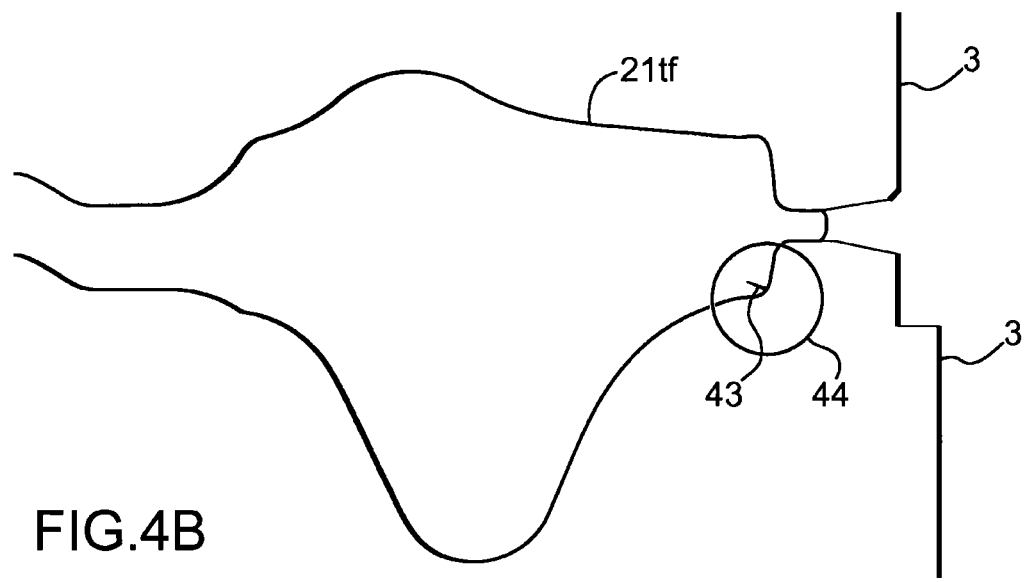

At step E2, after a fault has been detected in a defective forged component (see FIG. 4A), the processing means 15 add a fault plotter 43 to the final model 21f in a zone corresponding to the fault region of the defective forged component 1f to obtain a final plotted model 21tf (see FIG. 4B).

FIG. 4A is an example illustrating part or more specifically one half of a defective forged component 1tf having a forging lap 33 (e.g. a small crack) seen in a micrographic cross-section of the component 1. In addition, FIG. 4B gives a 2D illustration of the corresponding part of the final plotted model 21tf integrating the fault plotter 43 in a zone 44 corresponding to the fault region 34 of the defective forged component 1tf in FIG. 4A.

Figure 4C:
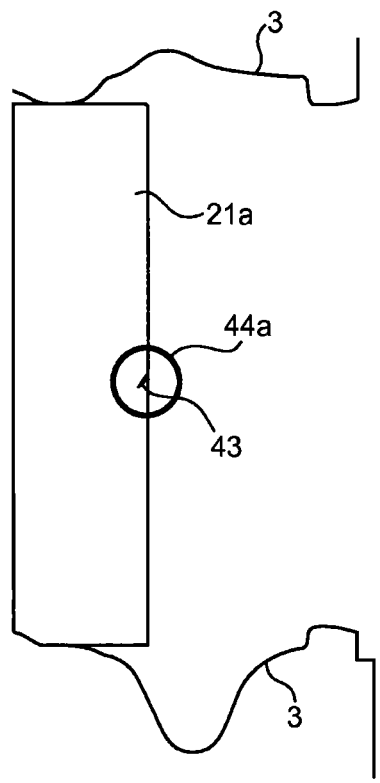
Figure 4D:
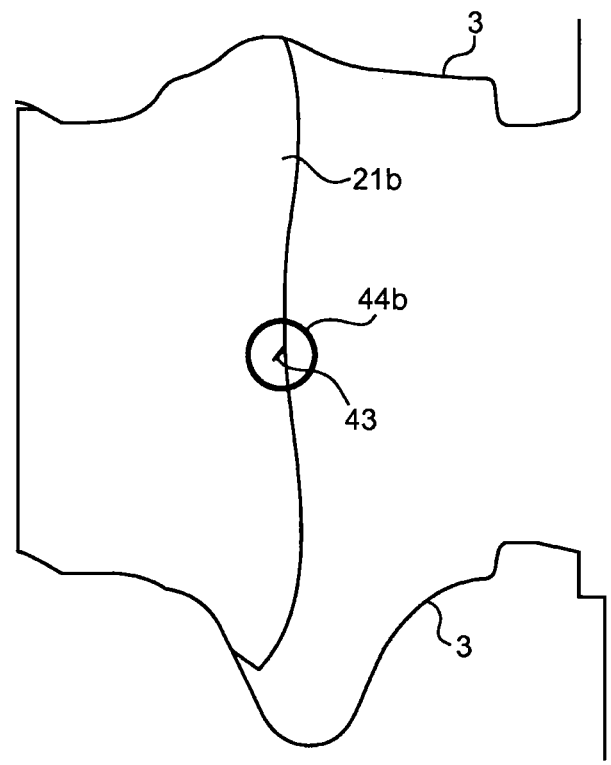

At step E3, the processing means 15 together with the viewing means 20 allow the tracking in time of the fault plotter 43 by reversing the kinetics (i.e. by reversing the sequence of modelling) starting from the final plotted model 21tf to identify the origin of the fault in the defective forged component 1tf (see FIGS. 4C and 4D). It is thus possible to track the history of the region which suffered the defect.

When modelling the forging operation, the polygon mesh 23 of the model 21 representing the component 1 becomes deformed over time. In other words, the relative positions of the nodes 25 are modified in relation to one another during the transformation. This generates variations in the expanse and location of the fault plotter 43 which is defined in relation to neighbouring nodes 25 whose coordinates are known at each modelling step. Therefore, by going back in time, it is possible to identify the morphology, geometry and position of the fault 33 before flattening of the component 1.

It will be noted that the fault 33 may result from an original flaw in the material of the blank 1a, or from a defect related to forging parameters (working speed, temperature, etc.) or from a geometric defect of the component 1 and/or of the shaping tools 3.

FIG. 4C illustrates the locating of the fault plotter 43 in the initial model 21a. This allows identification of the region 44a in which the fault would have been if it had been contained in the blank 1a.

To identify other sources of the fault, the dynamic locating system 12 is used to locate the fault plotter 43 in intermediate models likely to induce the fault.

For example, FIG. 4D illustrates the locating of the fault plotter 43 in an intermediate model 21b having a particular configuration.

This intermediate model 21b shows that the fault plotter 43 is positioned in the vicinity of an area 44b of concavity normally generated by penetration of tooling 3 into the material of the component 1 to be forged.

Therefore an abnormally marked concavity or inflection in this zone 44b may be the cause of the lap or fault 33 in the defective component 1tf. It is noted that accentuation of the concavity may result for example from a parallelism defect between the dies or forging tools 3 and/or from poor centring of the blank 1a in relation to the centre of the tooling 3.

It is therefore of interest to model the different scenarios which generate accentuated concavity to diagnose or verify whether it is indeed the concavity which led to this fault 33.

For example, FIGS. 5A-5E illustrate the modelling of forging using a blank 21a that is deliberately offset from the tooling 3.

Figure 5A:
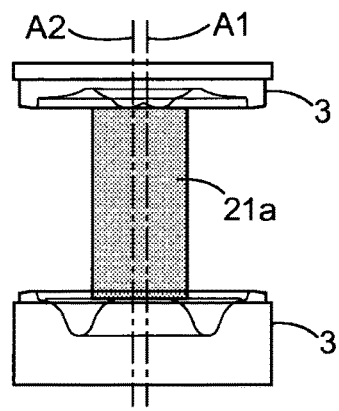
FIGS. 5A-5E illustrate modelling of the forging of a blank offset from the tooling.

FIG. 5A shows a blank 21a whose central axis A1 is offset by a few millimeters from the axis of symmetry A2 of the tooling 3.

Figure 5B:
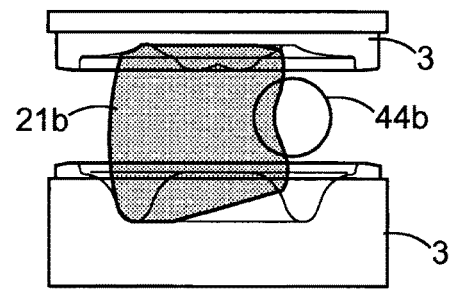
Figure 5C:
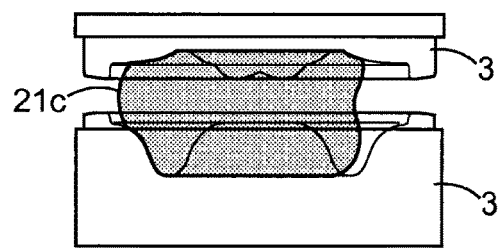
Figure 5D:
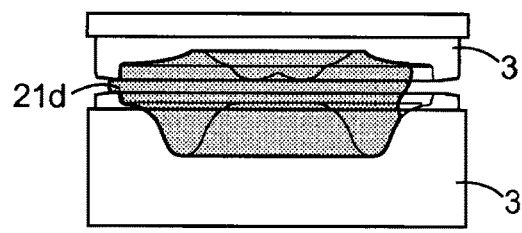
Figure 5E:
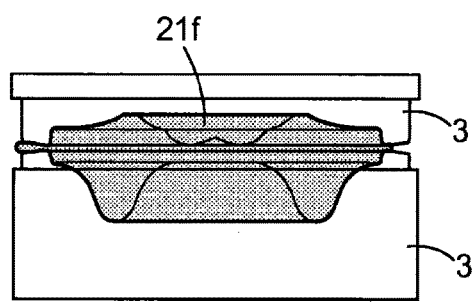

FIG. 5B clearly shows an increase in concavity in the zone 44b of original concavity in the vicinity of which the fault has been located. This clearly evidences a high risk of a lap formation in the concavity zone as illustrated in FIGS. 5C-5E. In particular, FIG. 5E shows that the final model 21f of the forged component is highly dissymmetric.

It is therefore possible to modify the configuration or geometry of the forging tools 3 so that the penetration of the two tool cores 3 into the component 1 no longer generates any concavity or that the flow of material occurs in different manner so that the concavity is reduced or eliminated.

In general, the locating of the origin of the fault 33 according to the invention allows the modelling of different effects or scenarios which may lead to the cause of the fault so that it can be remedied.

FIGS. 6 and 6A-6C illustrate a method for the dynamic locating of a fault detected in a defective component according to another embodiment of the invention.

According to this embodiment, the first model to which the fault plotter 44 is added corresponds to the initial model 21a representing the component before forging (the blank) 1a so that the first plotted model corresponds to an initial plotted model 21ta representing a defective blank 1ta.

At step E11, the processing means 15 model the shaping operation of a component by forging according to successive models comprising an initial model 21a corresponding to the component 1a before forging and a final model 21f corresponding to the forged component 1f.

Figure 6:
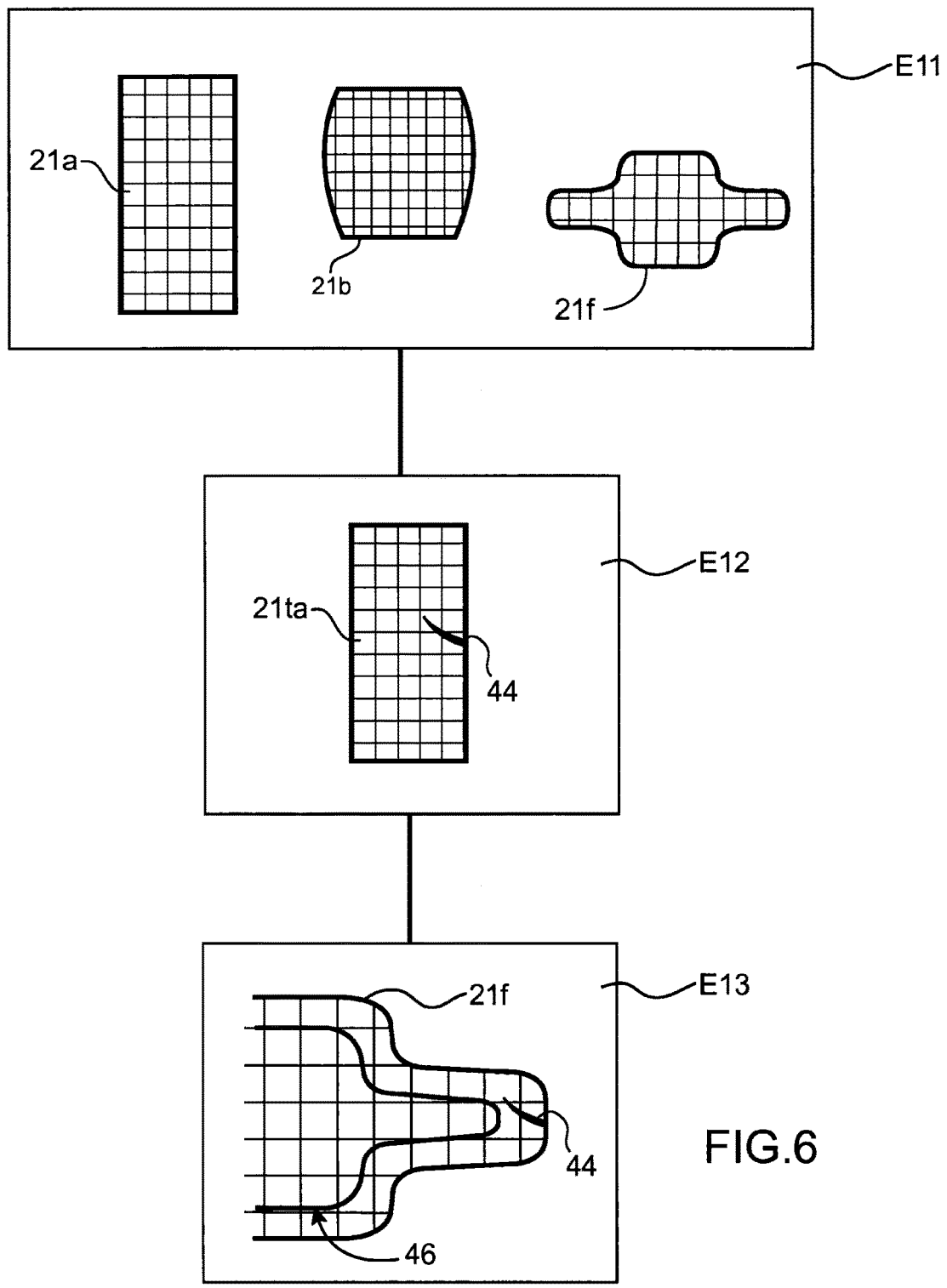
FIGS. 6 and 6A-6C illustrate a method for the dynamic locating of a fault observed in a defective component, according to another embodiment of the invention.
Figure 6A:
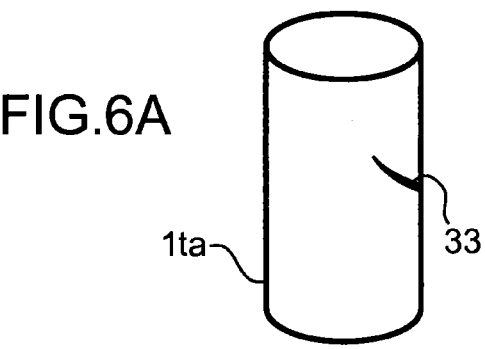
Figure 6B:
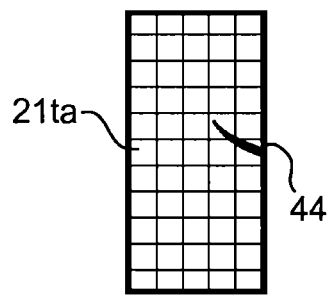

At step E12, after a fault 33 has been detected in a defective blank 1ta (see FIG. 6A), the processing means 15 add a fault plotter 44 to the initial model 21a in a zone corresponding to the region of the fault 33 in the defective blank 1ta, to obtain an initial plotted model 21ta (see FIG. 6B).

FIG. 6A is an example illustrating a defective blank 1ta having a small fault 33 on its surface and FIG. 6B gives a 2D illustration of the initial plotted model 21ta integrating the fault plotter 44 in a zone corresponding to the region of the fault 33 in the defective blank 1ta in FIG. 6A.

At step E13, the processing means 15 together with the viewing means 20 allow the locating of the fault plotter 44 in the final model 21f to verify whether the fault in the forged component lies outside a machining area 46 of this forged component. This allows economy of components by checking whether or not the forged component after machining will be impacted by the initial fault 33 of the component 1ta before forging.

Figure 6C:
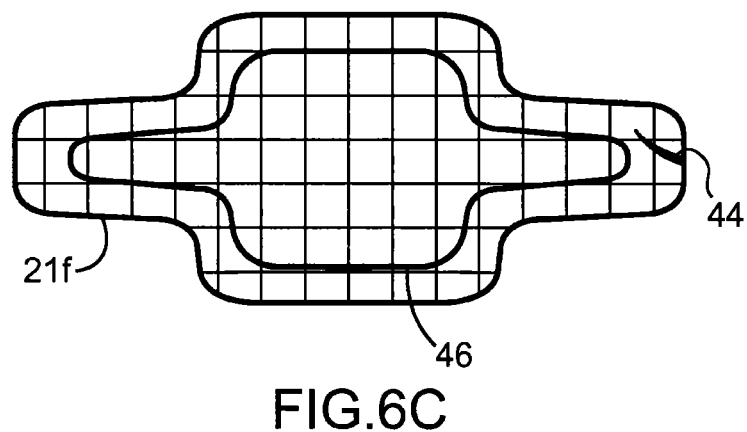

FIG. 6C illustrates the locating of the fault plotter 44 in the final model and the machining contour 46. This example shows that the fault does not affect the finished component after machining and therefore the starting blank can be used.

The invention claimed is:

1. A system for dynamic diagnosis of a fault observed in a component obtained after a forging operation of a blank, the system comprising:
   a processor configured to:
      model the forging operation by modelling working of the component during the forging operation as a function of forging parameters, the modeling leading to a set of time successive models of forming of the component during the forging operation, the set comprising an initial model corresponding to the blank, intermediate models corresponding to intermediate forging operations, and a final model corresponding to the forged component, input data relating to a fault observed in the component, the component having a fault being a defective component, add a fault plotter to a first model belonging to the set of models, in a zone corresponding to a region of the fault in the defective component, to obtain a first plotted model representing the defective component at a time of detection of the fault, and track the fault plotter over time during the modelling starting from the first plotted model, retrospectively or prospectively, to diagnose dynamics of the fault.

2. The system according to claim 1, wherein dimensions and positioning of the zone associated with the fault plotter in the first plotted model are substantially similar to dimensions and positioning of the region of the fault in the defective component.

3. The system according to claim 1, wherein the modelling of the forging operation is dynamic modelling with finite elements forming a polygon mesh at each iteration representing the component at the corresponding forging operations.

4. The system according to claim 3, wherein the processor is configured to define at each iteration dimensions and position of the fault plotter as a function of elementary elements of the polygon mesh at the operation in time.

5. The system according to claim 3, wherein the fault plotter is a contrast element associated with the polygon mesh.

6. The system according to claim 1, wherein the first model corresponds to the final model and the first plotted model corresponds to a final plotted model, and the processor is configured to track in time the fault plotter by reversing a sequence of the modelling starting from the final plotted model.

7. The system according to claim 6, wherein the processor is configured to locate the fault plotter in the initial model to identify the region in which the fault would have been in the component before forging.

8. The system according to claim 6, wherein the processor is configured to locate the fault plotter in the intermediate models comprising particular configurations to verify whether the particular configurations are likely to cause the fault.

9. The system according to claim 1, wherein the first model corresponds to the initial model and the first plotted model corresponds to an initial plotted model, and the processor is configured to locate the fault plotter in the final model to verify whether the fault in the forged component lies outside a machining region of the forged component.

10. The system according to claim 1, wherein the processor is configured to determine whether the fault is isolated or reproducible on a series of components to perform corrective action to avoid the reproduction of the fault.

11. The system according to claim 1, wherein the processor is configured to locate an origin of the fault.

12. A method for dynamic diagnosis of a fault observed in a component obtained after a forging operation of a blank, the method comprising:

modelling, using a processor, the forging operation by modelling working of the component during the forging operation as a function of forging parameters, the modelling leading to a set of time successive models of the forming of the component during the forging operation, the set comprising an initial model corresponding to the blank, intermediate models corresponding to intermediate forging operations, and a final model corresponding to the forged component;

obtaining data relating to a fault observed in the component, the component having a fault being a defective component;

adding a fault plotter to a first model belonging to the set of models using the processor, in a zone corresponding to a region of the fault in the defective component to obtain a first plotted model representing the defective component at a time of detection of the fault; and tracking the fault plotter in time during the modelling starting from the first plotted model, retrospectively or prospectively, to diagnose dynamics of the fault.

* * * * *